United States Patent
Chappa

(10) Patent No.: US 8,459,310 B2
(45) Date of Patent: Jun. 11, 2013

(54) SYSTEMS AND METHODS FOR FILLING MEDICAL DEVICE LUMEN

(75) Inventor: Ralph A. Chappa, Ham Lake, MN (US)

(73) Assignee: SurModics, Inc., Eden Prairie, MN (US)

(*) Notice: Subject to any disclaimer, the term of this patent is extended or adjusted under 35 U.S.C. 154(b) by 992 days.

(21) Appl. No.: 12/507,865

(22) Filed: Jul. 23, 2009

(65) Prior Publication Data
US 2010/0018602 A1  Jan. 28, 2010

Related U.S. Application Data

(60) Provisional application No. 61/083,301, filed on Jul. 24, 2008.

(51) Int. Cl.
*B65B 1/04* (2006.01)

(52) U.S. Cl.
USPC ........ 141/2; 141/5; 141/18; 141/37; 604/403; 604/416

(58) Field of Classification Search
USPC ............ 141/2, 5, 18, 37–38, 67, 70; 604/403, 604/416
See application file for complete search history.

(56) References Cited

U.S. PATENT DOCUMENTS

| | | | |
|---|---|---|---|
| 3,656,517 A | 4/1972 | Taylor et al. | |
| 4,949,766 A * | 8/1990 | Coatsworth | 141/67 |
| 5,018,909 A * | 5/1991 | Crum et al. | 406/138 |
| 5,222,529 A | 6/1993 | Zoltan et al. | |
| 5,516,522 A | 5/1996 | Peyman et al. | |
| 5,579,588 A * | 12/1996 | Reh et al. | 34/359 |
| 5,826,633 A | 10/1998 | Parks et al. | |
| 6,620,243 B1 * | 9/2003 | Bertellotti et al. | 118/621 |
| 6,684,917 B2 * | 2/2004 | Zhu et al. | 141/18 |
| 6,719,750 B2 | 4/2004 | Varner et al. | |
| 6,805,175 B1 * | 10/2004 | Pinkas et al. | 141/130 |
| 6,810,929 B1 * | 11/2004 | Tansey et al. | 141/231 |
| 6,889,723 B2 * | 5/2005 | Gerresheim et al. | 141/38 |
| 6,968,869 B2 * | 11/2005 | Eckhardt | 141/38 |
| 7,134,459 B2 * | 11/2006 | Carlson et al. | 141/130 |
| 7,854,242 B2 * | 12/2010 | Stehle | 141/38 |
| 7,878,430 B2 * | 2/2011 | Zhu et al. | 241/19 |
| 8,104,521 B2 * | 1/2012 | Luchinger et al. | 141/83 |
| 8,104,702 B2 * | 1/2012 | Zhu et al. | 241/60 |
| 8,230,887 B2 * | 7/2012 | Poole et al. | 141/2 |
| 2004/0043042 A1 | 3/2004 | Johnson et al. | |
| 2005/0019371 A1 | 1/2005 | Anderson et al. | |
| 2007/0160648 A1 | 7/2007 | Ashton et al. | |

* cited by examiner

*Primary Examiner* — Gregory Huson
*Assistant Examiner* — Nicolas A Arnett
(74) *Attorney, Agent, or Firm* — Pauly, Devries Smith & Deffner, L.L.C.

(57) ABSTRACT

The invention relates to systems and methods for filling a medical device with an active agent composition. In an embodiment, the invention includes a method for filling a medical device with an active agent composition. The method can include applying the active agent composition to the outside surface of the medical device, the medical device comprising a housing defining a lumen and a plurality of apertures. The method can also include contacting a surface of a press member against the outside surface of the medical device thereby pushing the active agent composition through the apertures and into the lumen of the medical device. Other embodiments are also included herein.

5 Claims, 11 Drawing Sheets

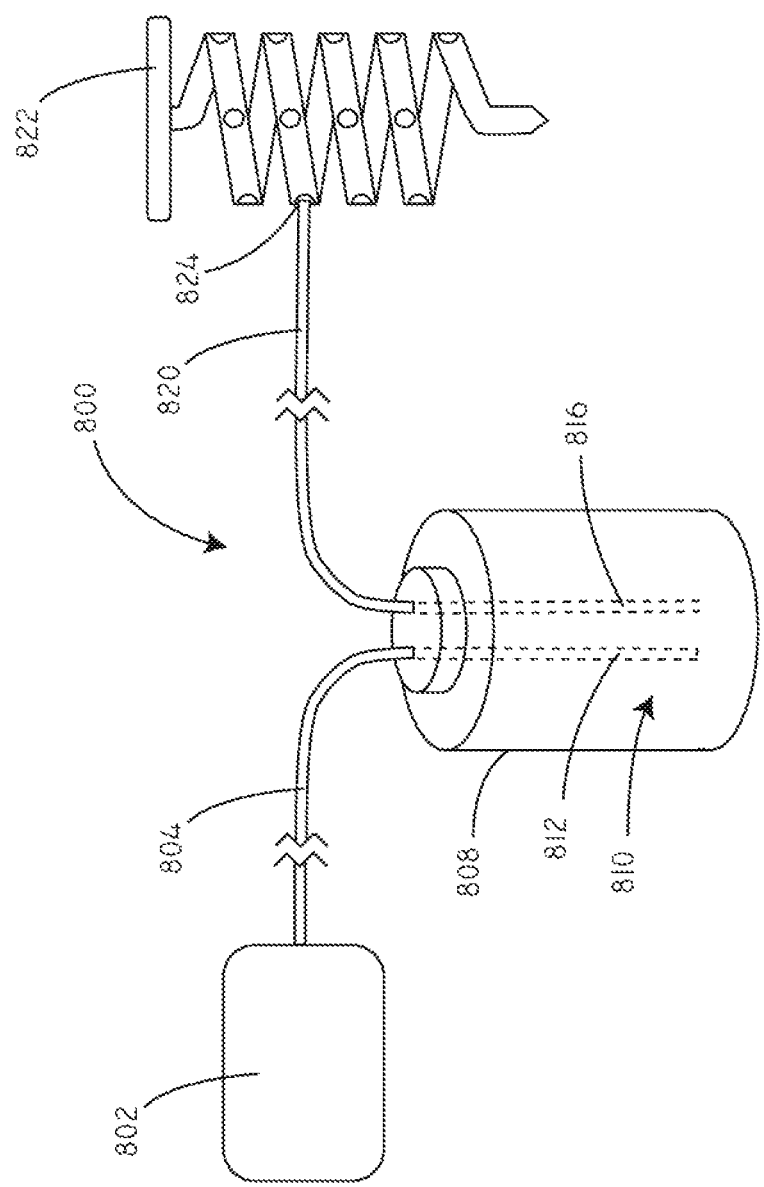

SYSTEMS AND METHODS FOR FILLING MEDICAL DEVICE LUMEN

This application claims the benefit of U.S. Provisional Application No. 61/083,301, filed Jul. 24, 2008, the contents of which are herein incorporated by reference.

FIELD OF THE INVENTION

The invention relates to systems and methods for making medical devices. More specifically, the invention relates to systems and methods for filling a lumen of a medical device.

BACKGROUND OF THE INVENTION

Therapeutic benefits can be realized by administering an active agent to a subject over an extended period of time. To this end, controlled-release drug delivery systems have been developed to control the rate of delivery of an active agent to a subject. Site-specific drug delivery can also offer therapeutic benefits. Site-specific drug delivery refers to the delivery of an active agent to a specific target tissue site, instead of systemically. Site-specific drug delivery offers advantages because the effect of the active agent on the target tissue can be enhanced while side effects of the active agent on other tissues can be reduced.

One technique for providing controlled-release site-specific drug delivery is to elute a desired active agent from a medical device. Devices used to provide controlled-release site-specific drug delivery can include medical devices wherein an active agent is eluted from a reservoir or lumen. Such medical devices are valuable tools in treating various disease states. However, they can be difficult to manufacture. In particular, the accurate and reproducible loading of a lumen with an active agent can be a difficult task.

As such there is a need for systems and methods for filling the lumen of a medical device in a manner that is accurate and reproducible.

SUMMARY

The invention relates to systems and methods for filling a medical device with an active agent composition. In an embodiment, the invention includes a method for filling a medical device with an active agent composition. The method can include applying the active agent composition to the outside surface of the medical device, the medical device comprising a housing defining a lumen and a plurality of apertures. The method can also include contacting a surface of a press member against the outside surface of the medical device thereby pushing the active agent composition through the apertures and into the lumen of the medical device.

In an embodiment, the invention can include a system for filling the lumen of a medical device with an active agent. The system can include a tube having a first end and a second end. The system can also include an actuation member having a surface that is flat in at least one direction, the actuation member configured to contact the tube. The system can also include a drive unit coupled to the actuation member, the drive unit configured to move the actuation member back and forth causing the tube to roll back and forth.

In an embodiment, the invention can include a method of loading a medical device with an active agent. The method can include placing a medical device into a vessel, the medical device comprising an internal lumen and an exterior surface, the exterior surface defining a plurality of apertures connecting the internal lumen with the exterior surface. The method can also include placing an active agent composition into the vessel. The method can also include moving the vessel sufficiently to cause repeated contact between the medical device and the interior surface of the vessel, wherein such movement results in the active agent composition being forced into the internal lumen through the plurality of apertures.

In an embodiment, the invention can include a system for filling the lumen of a medical device with an active agent. The system can include a vessel having a wall member. The system can also include a drive unit coupled to the vessel, the drive unit configured to cause the vessel to move. The system can also include an active agent composition disposed within the vessel. The system can also include a medical device disposed within the vessel, the medical device having a housing defining a lumen, the housing having an exterior surface, the housing defining a plurality of apertures connecting the lumen with the exterior surface.

In an embodiment, the invention can include a method of filling a medical device with an active agent. The method can include fluidizing a particulate active agent in a stream of air to form an active agent stream. The method can also include channeling the active agent stream into a lumen within the medical device. The method can also include allowing air from the active agent stream to escape the cavity while trapping the particulate active agent therein.

In an embodiment, the invention can include a system for filling the lumen of a medical device with an active agent. The system can include an air supply source. The system can also include a fluidization chamber in fluid communication with the air supply source. An active agent composition can be disposed within the fluidization chamber. The system can include a conduit in fluid communication with the fluidization chamber. The system can also include a medical device comprising a housing defining a lumen, the housing having an exterior surface, the housing defining a plurality of apertures connecting the lumen with the exterior surface, the medical device in fluid communication with the conduit.

The above summary of the present invention is not intended to describe each discussed embodiment of the present invention. This is the purpose of the figures and the detailed description that follows.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Some types of medical devices include a lumen (or reservoir) to hold an active agent that is then released within the body of a patient after implantation. The process of filling the lumen with the active agent can be difficult because of the need for accuracy and reproducibility in terms of the amount of the active agent loaded into the device. The filling process can also be complicated by the need to retain sufficient activity of the activity agent despite the sometimes harsh physical conditions associated with manufacturing processes.

Some medical devices also include a plurality of ports or apertures connected to a lumen through which the active agent can elute after the medical device is implanted in a subject. In general, these apertures are relatively small so as to control the elution rate of the active agent from the lumen.

In some circumstances, the apertures may be the only practical way to access the lumen during the manufacturing process. In these circumstances, the lumen must be filled by passing the active agent through the apertures and into the lumen. However, filling a lumen through a plurality of small apertures in an accurate and reproducible way presents a manufacturing challenge.

Figure 1:
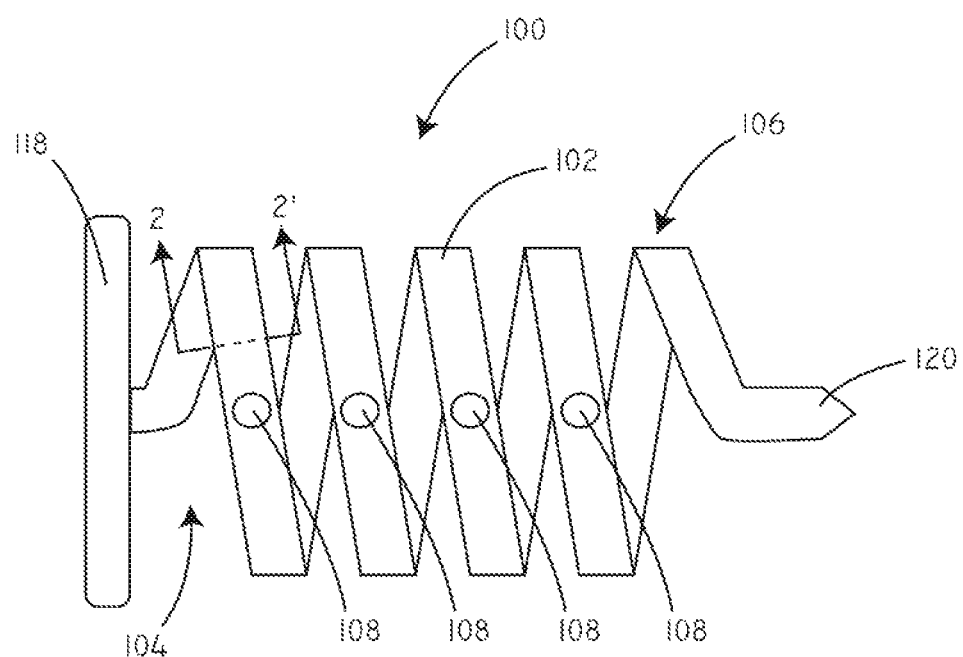
FIG. 1 is a schematic perspective view of a medical device in accordance with an embodiment herein.
Figure 2:
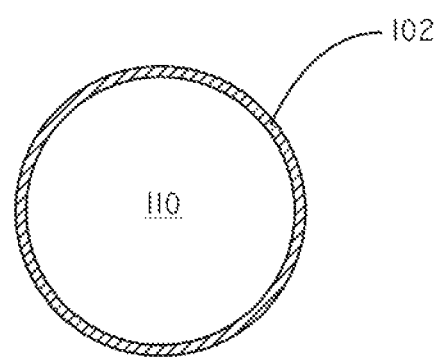
FIG. 2 is a cross-sectional schematic view of a medical device as taken along line 2-2' of FIG. 1.

A schematic perspective view of a medical device 100 including a lumen and a plurality of apertures is illustrated in FIG. 1. The medical device 100 includes a body member 102 having a proximal end 104 and a distal end 106. The medical device 100 can include a cap 118 and a tip 120. The body member 102 can be in a coiled configuration. The body member 102 can include a housing wall defining a plurality of apertures 108 (or ports). The body member 102 can have a lumen (or reservoir). The apertures 108 are configured to provide fluid communication between the outside of the device 100 and the lumen of the device 100. In some embodiments, the apertures 108 alone provide fluid communication between the lumen and the outside of the device. As such, filling the lumen requires passing the active agent in through the apertures 108 which can be difficult. FIG. 2 is a cross-sectional schematic view of the medical device 100 of FIG. 1 as taken along line 2-2' of FIG. 1. This view shows the housing wall of the body member 102 surrounding the lumen 110. Further exemplary medical devices are disclosed in U.S. Pat. No. 6,719,750 and U.S. Publ. Pat. App. No. 2005/0019371 the contents of all of which are herein incorporated by reference.

Embodiments of the invention include systems and methods for filling lumens of medical devices with active agent compositions in an accurate and reproducible way. In various embodiments, an active agent composition is brought into contact with the apertures on the lumen of a medical device and then the active agent composition is pushed through the apertures and into the lumen.

It has been found that embodiments of systems and methods described herein allow the loading of an active agent composition into a medical device lumen to be remarkably high in comparison to the theoretical maximum. For example, loading of active agent compositions can exceed 90% of the theoretical maximum loading in some embodiments. Various embodiments of systems and methods herein also allow active agent loading to be remarkably consistent and accurate. Aspects of exemplary embodiments will now be described in greater detail.

Figure 3:
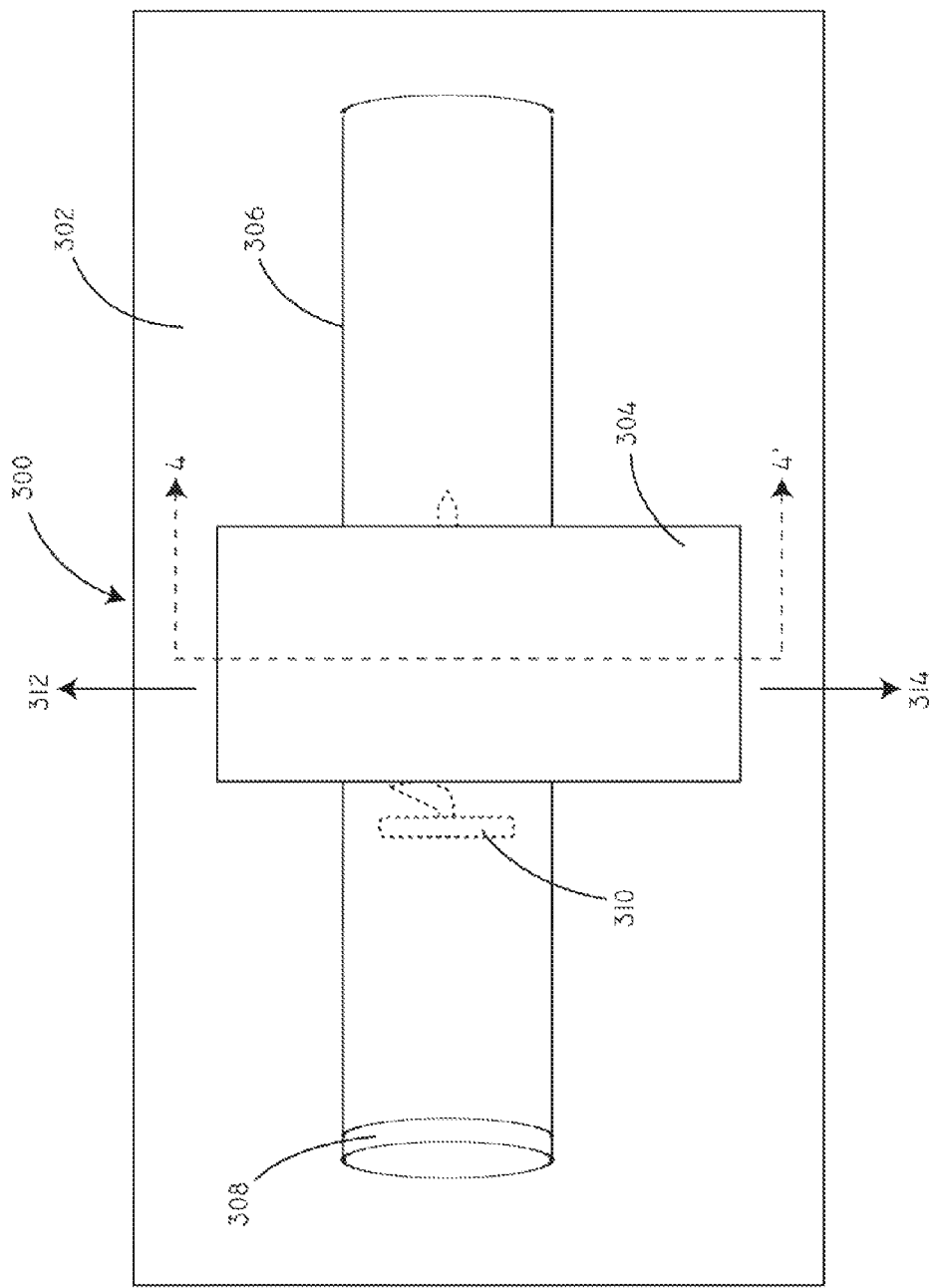
FIG. 3 is a schematic perspective view of a filling system in accordance with an embodiment herein.

Referring now to FIG. 3, a schematic perspective view of a filling system 300 is shown in accordance with an embodiment herein. The filling system includes a base plate 302 and an actuation plate 304. The base plate 302 can be substantially flat. In various embodiments the actuation plate 304 can be flat. However, in some embodiments the actuation plate 304 can be curved. In some embodiments, the base plate 302 and/or the actuation plate 304 can be made of a material such as, but not limited to, a metal, a polymer, or a ceramic.

Between the base plate 302 and the actuation plate 304 is a tube 306. In some embodiments, the tube 306 can be referred to as a press member. In some embodiments the tube 306 can be made of a deformable material such as a flexible polymer. Exemplary polymers can include polyurethane, polyethylene, polypropylene, and polysiloxane. In the embodiment shown, the tube 306 has a cap 308 or plug disposed on one end. In some embodiments, the tube 306 may lack a cap 308 but include other features for closing the ends of the tube. For example, in some embodiments, a clip or similar device can be used to close the ends of the tube.

A medical device 310 can be disposed inside of the tube 306 along with an active agent composition. Exemplary active agent compositions are described in greater detail below. After the medical device 310 and the active agent composition are put into the tube 302, the ends of the tube can be sealed, such as with a cap or a clip.

Figure 4:
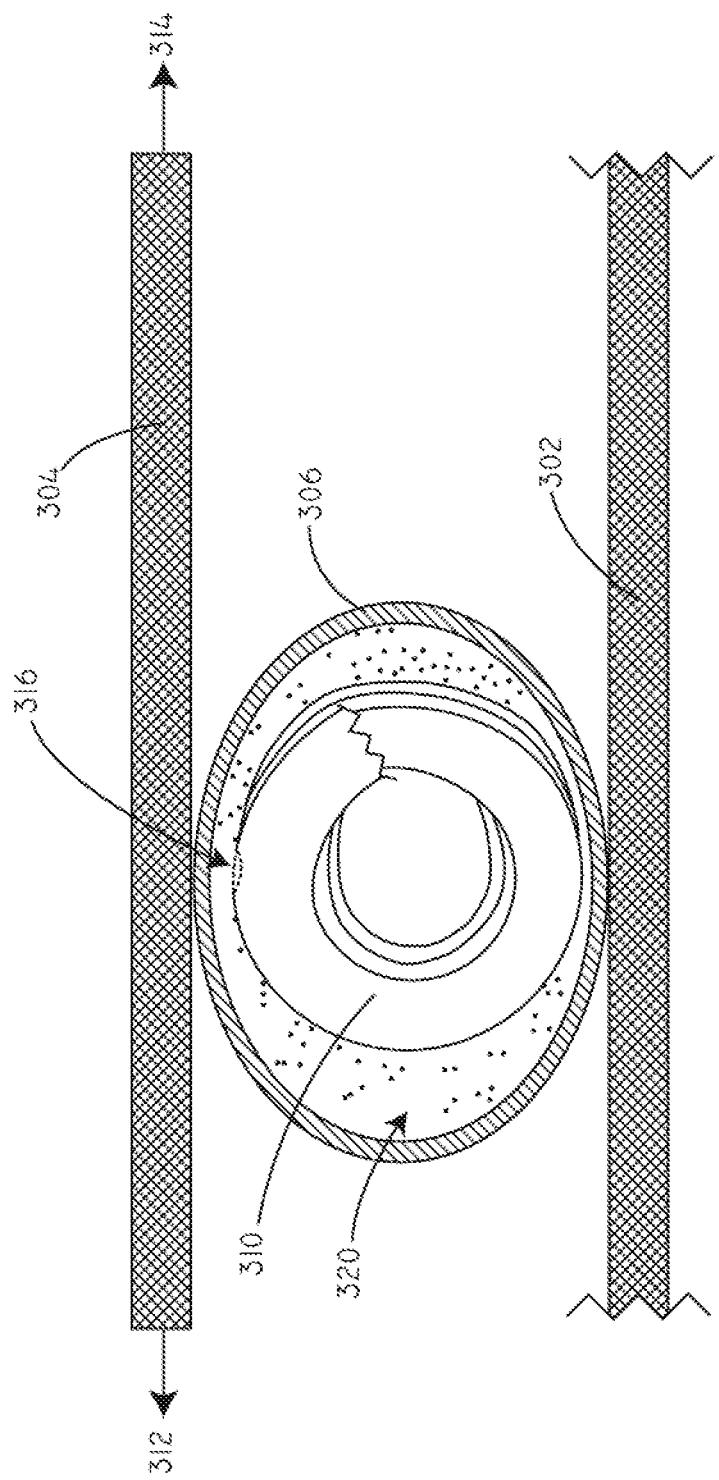
FIG. 4 is a cross-sectional schematic view of a filling system as taken along line 4-4' of FIG. 3.

Then the active agent composition can be put through the apertures into the lumen with a back and forth rocking motion. This process is illustrated with respect to FIG. 4. FIG. 4 is a cross-sectional schematic view of a filling system as taken along line 4-4' of FIG. 3. The medical device 310 includes an aperture 316 that provides fluid communication between the lumen 320 of the tube 306 and the lumen (not shown in this figure) of the medical device 310. The actuation plate 304 can exert a downward force on the tube 306. The tube 306 can deform in response to this downward force causing the tube to contact or nearly contact the medical device 310.

The actuation plate 304 can be configured to move back and forth in the direction of arrows 312 and 314. This causes the tube 306 and the medical device 310 within the tube 306 to roll back and forth. Based on this back and forth rolling motion, the active agent composition (represented in this view as particles 318) can, in turn, be positioned adjacent to the aperture 316 and then pushed into the lumen of the medical device 310. In other words, as the actuation plate 304 rolls the tube 306 and its contents back and forth, some of the active agent composition inevitably becomes at least transitorily aligned with the aperture 316 of the medical device. When this occurs and when the aperture 316 comes in contact with the inner surface of the tube, the resulting pressure on the active agent composition forces it into the lumen of the medical device 310 through the aperture 316.

Once inside the lumen of the medical device 310, it is believed that the active agent composition continues to move deeper into the lumen of the device because of the back and forth motion through a process similar to diffusion. As the actuation plate 304 continues to move back and forth, gradually more of the active agent composition becomes aligned with the aperture 316 and is pushed into the lumen of the medical device, filling it over time. In some embodiments, the actuation plate 304 is moved back and forth for at least about one minute. In some embodiments, the actuation plate 304 is moved back and forth for at least about five minutes. In some embodiments, the actuation plate 304 is moved back and forth for at least about twenty minutes.

Figure 5:
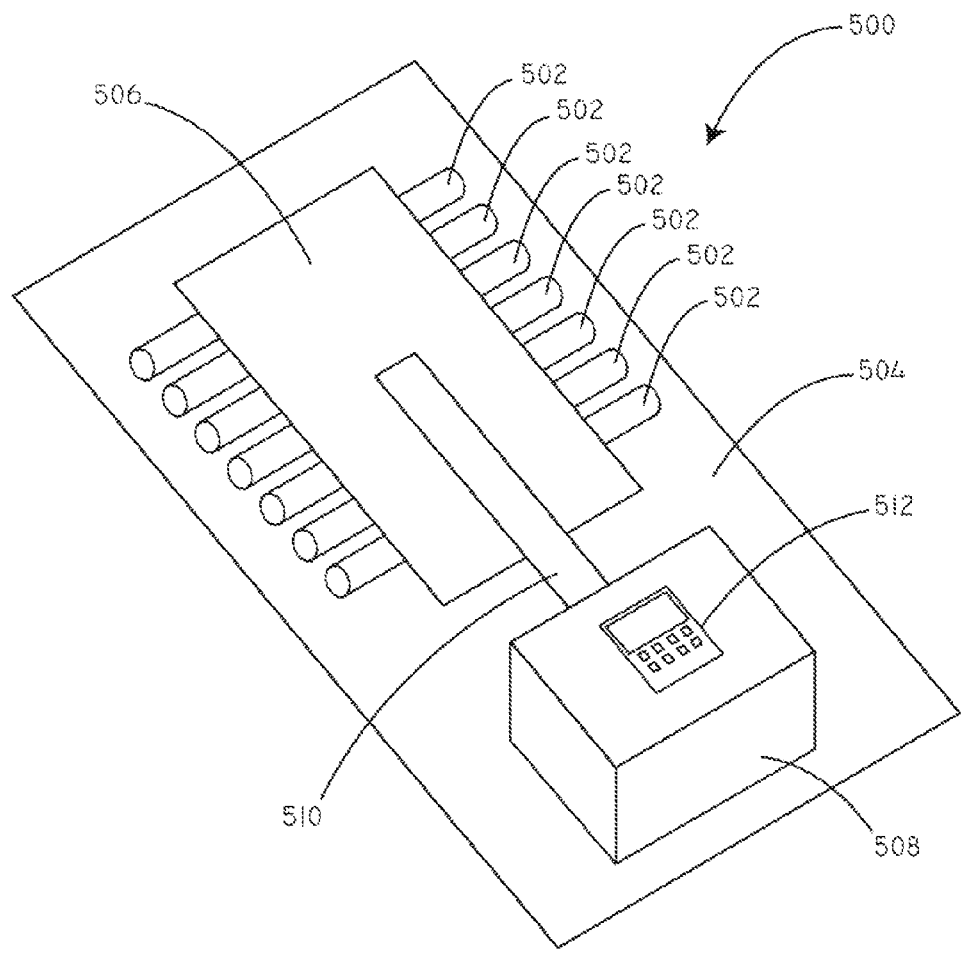
FIG. 5 is a schematic perspective view of a filling system in accordance with another embodiment of the invention.

It will be appreciated that in some embodiments systems included herein can be used to fill multiple medical devices with an active agent composition at the same time. FIG. 5 is a schematic perspective view of a filling system 500 in accordance with another embodiment of the invention. In this embodiment, the system 500 includes a plurality of tubes 502 that are held against a base plate 504 by an actuation plate 506. The actuation plate 506 is coupled to a drive unit 508 through a connecting bar 510. The drive unit 508 can include a control unit 512 and can be configured to cause the actuation plate 506 to move back and forth over the tubes 502. This causes the tubes 502 and their contents to roll back and forth. The drive unit 508 can include an electrical motor in order to generate motive force. The control unit 512 can include a microprocessor (not shown) and can allow a user to specify the rate of moving the actuation plate 506 back and forth as well as the total time for moving the actuation plate 506.

Medical devices (shown in FIG. 6) and an active agent composition (not shown) can be disposed within the tubes. As the actuation plate 506 moves back and forth, the active agent composition can be filled into the lumen of the medical devices through the back and forth rolling motion illustrated in FIG. 4.

Figure 6:
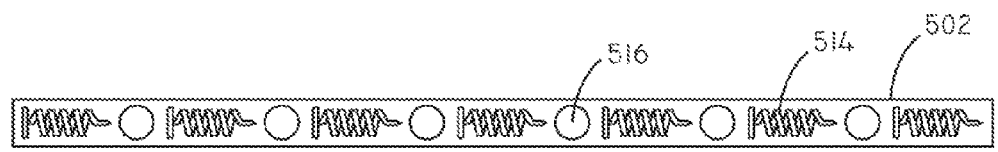
FIG. 6 is a cross-sectional schematic view of a component of a filling system in accordance with an embodiment of the invention.

FIG. 6 is a cross-sectional schematic view of one embodiment of the tubes 502 from FIG. 5. A plurality of medical devices 514 and, optionally, spacers 516 can be disposed within the tube 502, along with an active agent composition (not shown). As such, the system can be used to fill the lumens of a plurality of devices at the same time.

Figure 7:
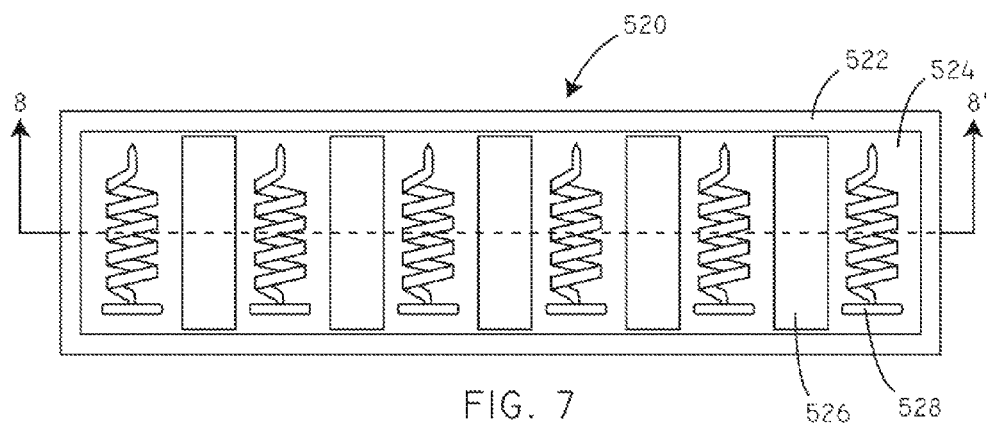
FIG. 7 is a schematic top view of a tray of a filling system in accordance with an embodiment of the invention.

In some embodiments of filling systems, medical devices can be disposed within trays instead of within tubes. Referring now to FIG. 7, a schematic top view is shown of a tray 520 of a filling system in accordance with an embodiment of the invention. The tray 520 includes a sidewall 522 and a base 524. In some embodiments, the base 524 is composed of a material that is deformable. Together, the sidewall 522 and the base 524 define a recessed portion of the tray 520, into which objects can be disposed. For example, a plurality of medical devices 528 and, optionally, a plurality of spacers 526 can be disposed within the tray 520. Also, an active agent composition can be disposed within the tray. The medical devices 528 can then be filled with the active agent composition through a back and forth rolling motion illustrated with respect to FIG. 8.

Figure 8:
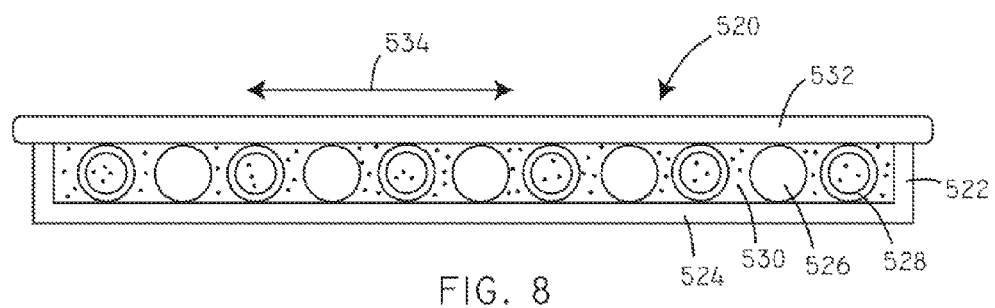
FIG. 8 is a schematic cross-sectional view of a tray of a filling system in accordance with an embodiment of the invention.

FIG. 8 is a schematic cross-sectional view of the tray 520 as taken along line 8-8' of FIG. 7. The active agent composition 530 can be disposed within the tray 520 along with the medical device 528 and, optionally, the spacers 526. An actuation plate 532 can be disposed over the tray 520. The actuation plate 532 can be moved back and forth in the direction of arrow 534, thereby causing the medical devices 528 to roll back and forth within the tray. This back and forth rolling action causes some of the active agent to become aligned with apertures on the medical devices 528 and then pushed into the lumen of the medical devices 528 through contact with either the actuation plate, the tray, or the spacers. As such, the lumens within the medical device 528 filled with the active agent composition 530 through a back and forth rolling action. In some embodiments, the actuation plate 532 can be deformable so as to contact the medical devices 528 and/or the spacers 526 as it is being moved back and forth. In some embodiments, the actuation plate can be moved back and forth by a drive unit (such as the drive unit 508 shown in FIG. 5).

Figure 9:
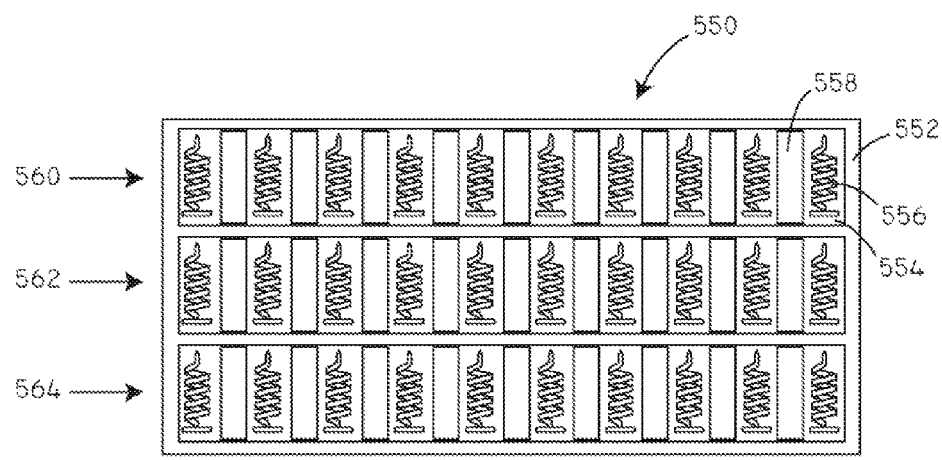
FIG. 9 is a schematic top view of a tray of a filling system in accordance with an embodiment of the invention.

It will be appreciated, that trays used with filling systems in accordance with embodiments herein can take on many different configurations. Referring now to FIG. 9, a schematic top view is shown of a tray 550 of a filling system in accordance with another embodiment of the invention. The tray 550 includes a sidewall 552 and a base 554 defining a recessed portion. In this view, a plurality of medical devices 556 and spacers 558 are disposed within the tray 550. The tray 550 defines a first row 560 to hold medical devices 556 and spacers 558, a second row 562, and a third row 564.

As shown in the examples below, it has been discovered that tumbling medical devices having apertures along with an active agent composition in an enclosure, such as in a rotary drum, results in the devices being filled with the active agent composition. Though this approach may result in slightly lower activity levels of active agents, such as proteins, because of physical trauma during tumbling, it can be effective to reproducibly fill medical devices such as the device illustrated in FIG. 1. Aspects of this type of filling method and related systems are described in greater detail with respect to FIGS. 10-12.

Figure 10:
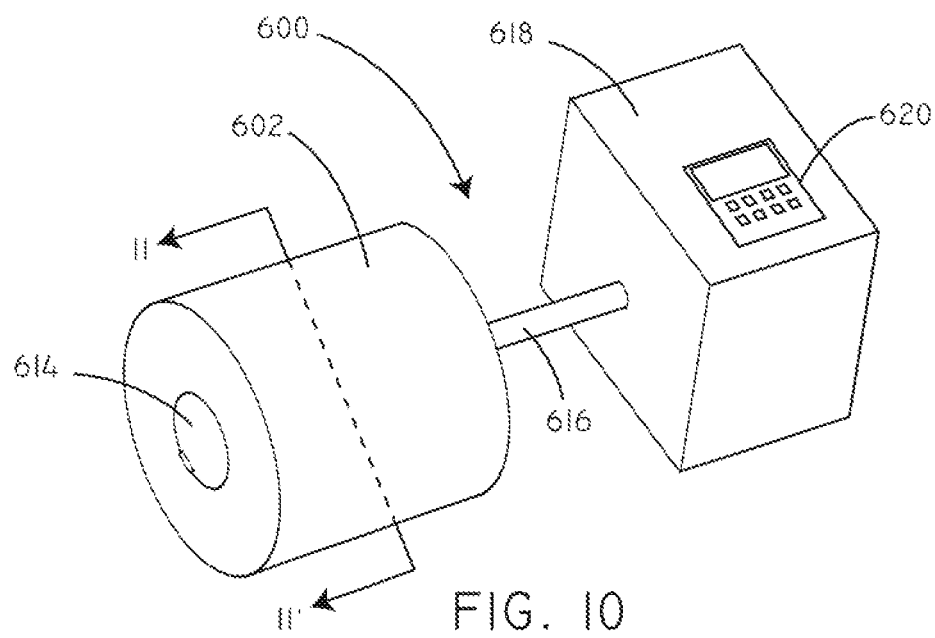
FIG. 10 is a schematic perspective view of a filling system in accordance with another embodiment of the invention.

FIG. 10 is a schematic perspective view of a filling system 600 in accordance with an embodiment of the invention. The filling system 600 includes a housing 602 that can be configured to be rotated, such as a rotary drum. The interior of the housing 602 can be accessed through a closable door 614. The housing 602 can be coupled to a drive unit 618 via a shaft 616. The drive unit 618 can include a motor, such as an electric motor. The drive unit 618 can include a control unit 620 in order to control the motion of the housing 602. For example, the control unit 620 can be configured by a user in order to control the characteristics of how the housing 602 is moved including rotation speed, rotation direction, and the like.

Figure 11:
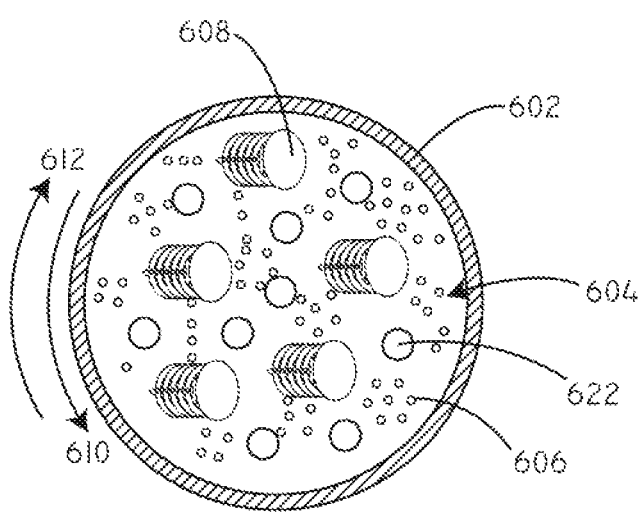
FIG. 11 is a schematic cross-sectional view of a filling system as taken along line 11-11' of FIG. 10.

FIG. 11 is a schematic cross-sectional view of the filling system 600 as taken along line 11-11' of FIG. 10. The housing 602 defines an interior volume 604. Medical devices 608 with lumens and apertures can be placed within the interior volume 604 along with an active agent composition 606 (represented in this view as particles), and milling media 622. The milling media 622 can take on various forms, such as ceramic beads, metal objects, polymer pellets, or the like. The housing 602 can be configured to rotate in the direction of arrow 610 or in the direction of arrow 612, or alternately in one direction and then the other. In the process of rotating the housing 602, the medical devices 608 tumble within the interior volume 604 contacting each other, the active agent composition 606, the milling media 622, and the inside surface of the housing 602. As is shown in the example below, such tumbling has been shown to effectively transfer the active agent composition 606 through the apertures and into the interior volume (or lumen) of the medical devices.

Figure 12:
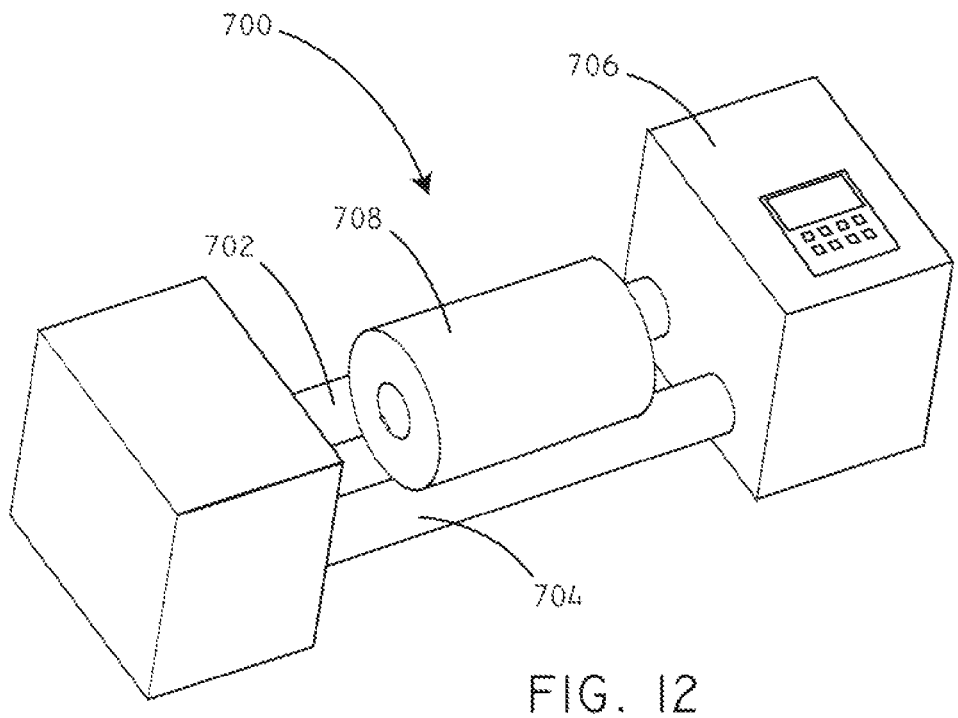
FIG. 12 is a schematic perspective view of a filling system in accordance with another embodiment of the invention.

It will be appreciated that filling systems used with a tumbling approach can take on various configurations. Referring now to FIG. 12, a schematic perspective view is shown of a filling system 700 in accordance with another embodiment of the invention. The filling system 700 includes a drive unit 706, a first roller 702, and a second roller 704. A housing 708 (or drum) is disposed on top of the first roller 702 and the second roller 704. The drive unit 706 can cause the first roller 702 and the second roller 704 to rotate back and forth. As the first roller 702 and second roller 704 rotate, the housing 708 will also rotate, thereby tumbling the contents of the housing 708. A plurality of medical devices, an active agent composition, and milling media can be disposed within the housing 708. The tumbling action causes the active agent composition to be filled into the lumens of the medical devices.

In accordance with various embodiments herein, a plug can be used when filling medical devices that have a helical configuration. The plug can occupy the inner diameter of the helical or corkscrew portion of a medical device, such that the helical portion is effectively wrapped around the plug (see FIG. 13). Using this type of plug in a filling method, such as in a rolling approach as described with respect to FIGS. 3-8, or in a tumbling approach as described with respect to FIGS. 10-12, can offer various advantages. For example, the use of a plug can help to maintain the structural integrity of the medical device during the filling operation. In addition, the use of a plug can help prevent medical devices from getting entangled with one another during a tumbling-type filling operation.

Figure 13:
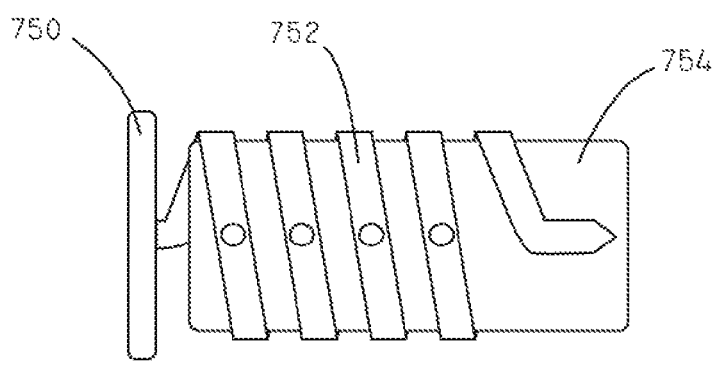
FIG. 13 is a schematic perspective view of a medical device with an inner diameter plug in accordance with another embodiment of the invention.

FIG. 13 is a schematic perspective view of a medical device 750 with a plug 754 in accordance with another embodiment of the invention. The medical device 750 includes a helical portion 752. The plug 754 fits into the helical portion 752 and can be held through a compression fit type mechanism. The plug 754 can be made of various materials including polymers, ceramics, metals, natural materials such as cork, and the like. After a filling operation, the plug 754 can then be removed from the helical or coiled portion of the medical device.

Figure 14B:
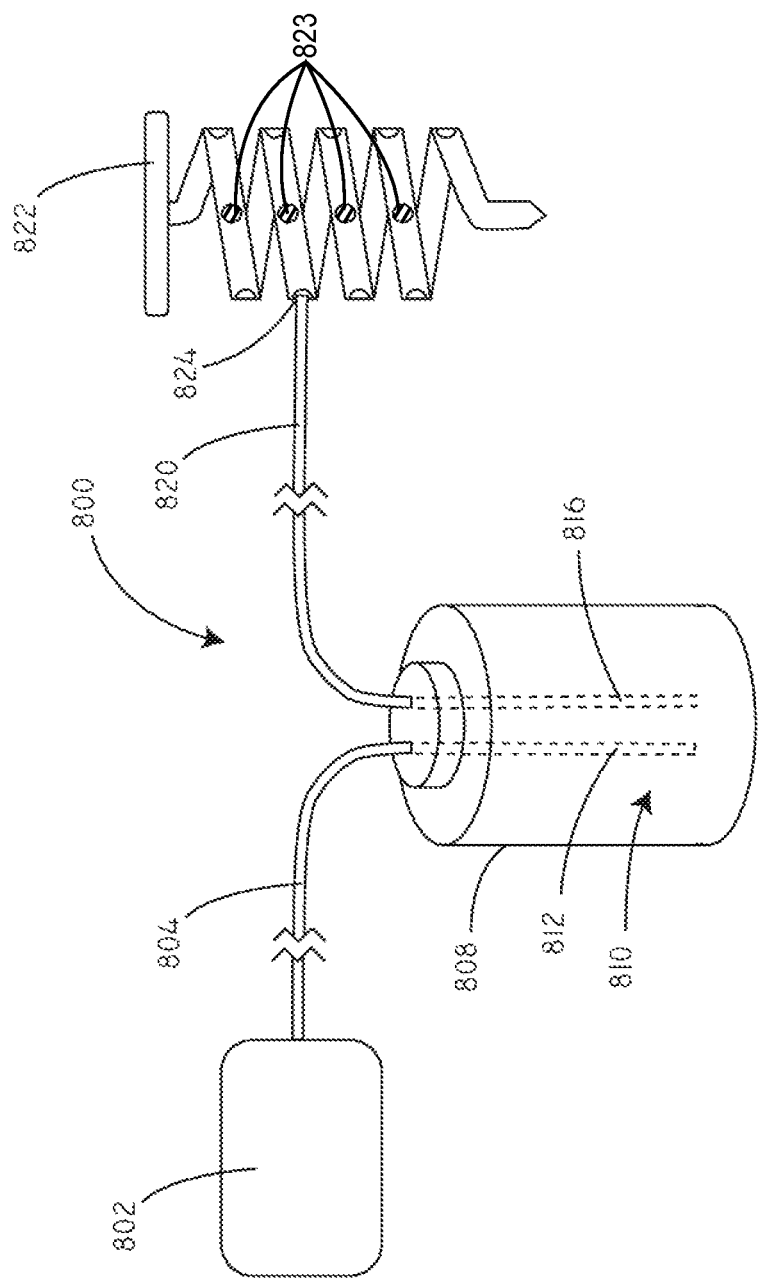
FIGS. 14A and B are a schematic perspective view of a filling system in accordance with another embodiment of the invention.

In some embodiments, active agent particles can be fluidized in a stream of air and then routed to a medical device for filling. Referring now to FIG. 14, a schematic perspective view of a filling system is shown in accordance with another embodiment of the invention. The filling system 800 includes an air supply source 802 in fluid communication with a first conduit 804. The first conduit 804 passes into a fluidization chamber 808. The fluidization chamber 808 has an interior volume 810 into which an active agent composition is disposed. As air is pumped through the first conduit 804 and through an inflow channel 812, the resulting turbulence within the fluidization chamber 808 causes the active agent composition to be mixed with the air and then carried along with the air into the outflow channel 816. The outflow channel 816 passes out of the fluidization chamber 808 becoming a second conduit 820. The second conduit 820 directs the flow of air and active agent particles into an aperture 824 of a medical device 822 that has a lumen and a plurality of apertures connecting the lumen to the outside. The active agent particles are then dropped by the flow of air within the lumen while the air passes out through the other apertures.

In some embodiments, some of the apertures on the medical device 822 can be at least partially occluded so as to block passage of the active agent particles while still allowing the flow of air. In some embodiments, this can be accomplished by fitting a porous sheath or mesh structure 823 over the apertures not receiving the incoming flow of particles from the second conduit 820.

Figure 15:
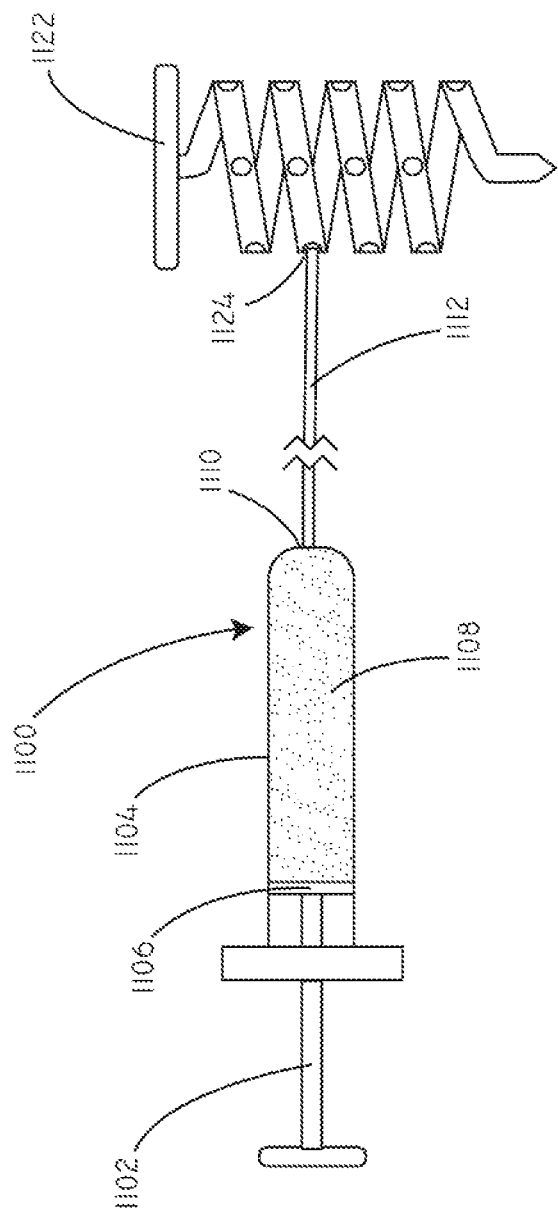
FIG. 15 is a schematic perspective view of a filling system in accordance with another embodiment of the invention.

FIG. 15 is a schematic perspective view of a filling system 1100 in accordance with another embodiment of the invention. The filling system 1100 includes a housing 1104 defining an interior volume 1108. Active agent particles are disposed within the interior volume 1108. A positive pressure is generated within the interior volume 1108 by movement of a piston 1106 coupled to a depressor 1102. At certain movement rates of the piston, an amount of turbulence is generated within the interior volume 1108 that is sufficient to fluidize the active agent particles within the air. The positive pressure then causes the fluidized active agent particles and air to pass through an orifice 1110 into a conduit 1112. The flow of active agent particles and air is then transferred into an aperture 1124 of a medical device 1122 that has a lumen (or reservoir) and a plurality of apertures connecting the lumen to the outside. The active agent particles are dropped by the flow of air within the lumen while the air passes out through the other apertures.

In some embodiments, a spray nozzle can also be utilized in a system for filling the lumen of a medical device. By way of example, a spray stream can be generated that includes an active agent composition. The spray stream can be aimed at the aperture of a lumen containing medical device. In such embodiments, the active agent composition may or may not include a solvent as it passes through the spray nozzle. In embodiments where it does include a solvent, the spray head can be configured such that solvents are substantially evaporated from the spray stream by the time it reaches the medical device to be filled. In some embodiments, a device such as a sand blasting system, can be used to produce a stream of particles that can be directed at an aperture of a medical device.

Figure 16:
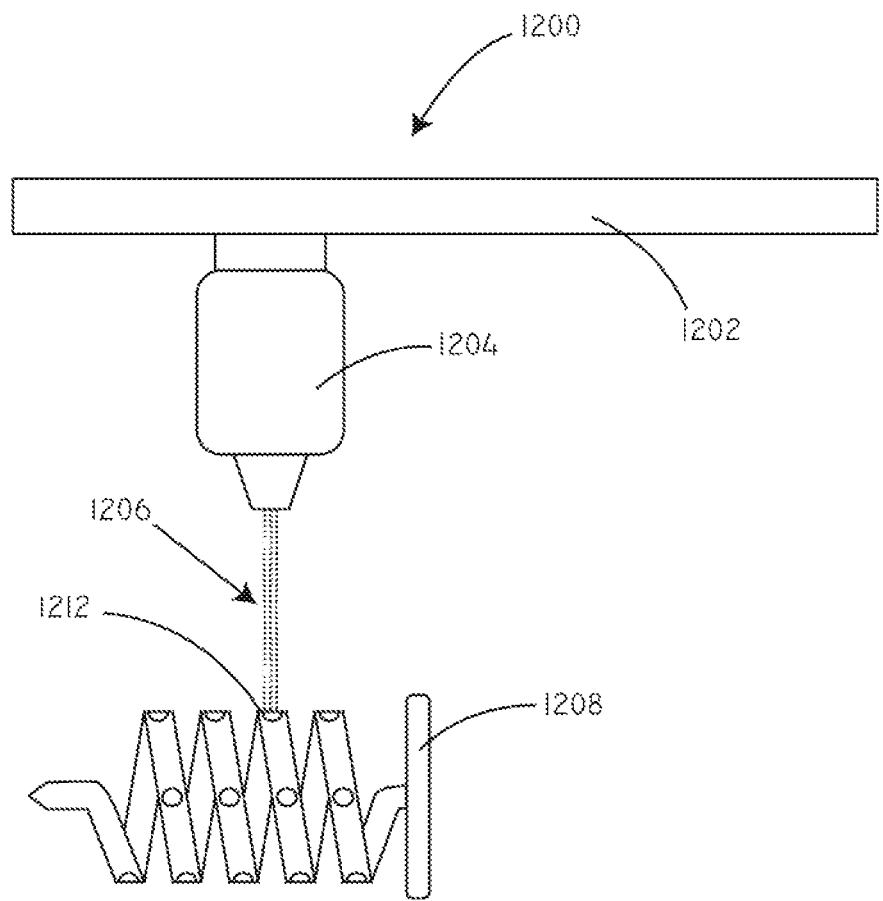
FIG. 16 is a schematic perspective view of a filling system in accordance with another embodiment of the invention.

Referring now to FIG. 16, a schematic perspective view of a filling system 1200 in accordance with another embodiment of the invention is shown. The filling system 1200 includes a spray head 1204 mounted on a support member 1202. The spray head 1204 generates a spray stream 1206 including an active agent composition. The spray stream 1206 can be directed at a medical device 1208. The system can be configured so that the spray stream 1206 consisting of substantially no solvents by the time the spray stream 1206 encounters the medical device 1208. The spray stream 1206 can be specifically directed at an aperture 1212 of the medical device 1208, such that the material of the spray stream 1206 passes into the lumen of the medical device 1208.

Active Agent Compositions

Active agent compositions as used with various embodiments herein can take on different forms. Such forms can include those where the active agent is in a particulate form, those where the active agent is part of a paste or slurry, and those where the active agent is part of an emulsion. In some embodiments, the active agent composition can be substantially dry (e.g., having no solvent), while in other embodiments a solvent can be included with the active agent composition.

In embodiments where the active agent composition is in the form of a particulate, the particles can be of a substantially uniform diameter. In other embodiments, the active agent can be more heterogeneous in terms of the diameter of particles. In some embodiments, the average diameter of particles in the active agent composition can be less than about 100 microns. In some embodiments, the average diameter of particles in the active agent composition can be less than about 50 microns.

In some embodiments, the active agent composition can be made into a particulate form through a milling process. Various types of milling process can be used including ball milling, jet milling, rod milling, SAG milling, grinding roll processing, buhrstone milling, and the like. In some embodiments, the average size of the particles in the active agent composition can be modified through milling processes such as those just described.

It will be appreciated that active agents can include proteins, nucleic acids, antibodies, antibody fragments, small molecules, and the like. Examples of active agents can specifically include thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, (poly)peptides, proteins, enzymes, extracellular matrix components, inhibitors, free radical scavengers, chelators, antioxidants, anti polymerases, antiviral agents, photodynamic therapy agents, and gene therapy agents.

In some embodiments, the active agent composition can include substantially all active ingredients. However, in other embodiments, non-active ingredients can also be included with the active agent composition. Non-active ingredients can include wetting agents, binders, bulking agents, carriers, excipients, stabilizers, and the like.

The present invention may be better understood with reference to the following examples. These examples are intended to be representative of specific embodiments of the invention, and are not intended as limiting the scope of the invention.

EXAMPLES

Example 1

Filling Lumens of Devices

A length of flexible polysiloxane tubing (3/16 inch outside diameter and 1/8 inch inside diameter) was obtained and cut into lengths of approximately four centimeters. One end of each of the pieces of the tube was then sealed with a clip.

A coiled metal device (similar to that shown in FIG. 1) having an internal lumen and a plurality of apertures (N=9) and sealed ends was weighed and then placed into the tubing. The apertures had a diameter of approximately 0.25 mm. The internal lumen of the medical device was estimated to have a volume of approximately 1.3-1.4 mm$^3$ (or 1.3-1.4 µl).

Tubular metal devices (N=15) having an internal lumen were weighed and placed in groups of five into separate pieces of the polysiloxane tubing. Each tubular metal device includes a plurality (N=20) apertures having a diameter of approximately 0.25 mm. The lumens of the tubular metal devices were estimated to have a volume of 1.3-1.4 mm$^3$ (the same as the coiled metal device).

A powdered lysozyme composition was also placed into each of the polysiloxane tubing pieces. The amount of the active agent composition added was sufficient to fill approximately half of the interior volume of the tube. Then the remaining end of each piece of polysiloxane tubing was then sealed with a clip.

Each piece of polysiloxane tubing was then placed on a flat surface. A flat piece of metal having a width of approximately 1-2 cm and a length of approximately 10 cm was then placed on top of each piece of the tubing. While maintaining substantially constant downward force, the piece of metal was moved back and forth so that the tubing pieces rolled back and forth. The force on the tubing pieces from the piece of metal was sufficient for the top of the tubing to deform and contact the coiled metal device or metal tubes held within.

Back and forth rolling movement was continued for approximately 0.5-1 minutes. After this time, each piece of tubing was opened and the device inside was removed. Visual inspection showed that each of the apertures on the devices appeared to be occluded by the lysozyme composition. The devices were all then weighed again. The results of the weighing are shown in Table 1 below. It was found that coiled metal device weighed approximately 1.232 mg more after the filling process. For the three groups of five metal tubes, it was found that they gained a weight of, on average, 1.367 mg, 1.371 mg, and 1.354 mg.

Based on the volume of the internal lumens, the maximum loading was roughly estimated to be about 1.4 mg. The data show that, on average, this loading method achieved a relatively high percentage of the estimated theoretical maximum loading. The data further show devices can be loaded consistently. As such, this example shows that rolling-type methods and systems in accordance with various embodiments herein can be used to effectively fill the lumen of a medical device to a high percentage of theoretical maximum loading.

Example 2

Filling the Lumen of Medical Devices with an Apparatus including a Rotating Vessel A filling system was set up similar to that shown in FIG. 12. The filling system included two parallel rollers and a drum on top of the rollers. The drum had a total volume of 20 ml.

Six hollow metal tubes with sealed ends (each having 20 holes with a diameter of 0.008 inches (≈0.203 mm)) and an estimated lumen volume of 1.4 mm$^3$ each were placed into the drum along with 10 ml of 0.25 inch ceramic cylinder milling media and 2-3 grams of triamcinolone acetonide powder.

The rotating drum unit was then sealed and set to rotate at a speed of approximately 70-90 rotations per minute for a time period of approximately 14 hours.

The rotating drum unit was then opened and the devices were removed. Visual inspection showed that each of the apertures on the devices appeared to be occluded by the triamcinolone acetonide powder. The devices were then weighed again. The results of the weighing are shown in Table 1 below.

| Metal Tube # | Weight Change |
| --- | --- |
| 1 | 1.326 mg |
| 2 | 1.323 mg |
| 3 | 1.305 mg |
| 4 | 1.312 mg |
| 5 | 1.277 mg |
| 6 | 1.308 mg |

The data show that a tumbling-type method and system can be used to effectively fill the lumen of a medical device.

Example 3

Filling the Lumen of Medical Devices with an Apparatus including a Fluidization Chamber A MICROBLASTER® sand blasting system was obtained from Comco, Inc. (Burbank, Calif.). The sand blasting system was loaded with free flowing 50 micron silica grit.

The sand blasting system was aimed at a hollow metal tube having five holes each of 0.01 inches in diameter. Specifically, the flow of the silica grit was aimed at one of the five holes and the other four holes were partially occluded.

The flow of the silica grit through the sand blasting system was initialized. The sand blasting system generated a consistent spray stream of the silica grit focused at one of the holes in the hollow metal tube. After a short period of time, the sand blasting system was stopped.

The hollow metal tube was visually inspected. It was discovered that the holes were now occluded by the silica grit. This example shows that the lumen of a hollow device can be filled with a filling system that produces a spray stream of a particulate material.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific embodiments and techniques. However, it should be understood that many variations and modifications may be made while remaining within the spirit and scope of the invention.

Further Embodiments

In an embodiment, the invention includes a method for filling a medical device with an active agent composition. The method can include applying the active agent composition to the outside surface of the medical device, the medical device comprising a housing defining a lumen and a plurality of apertures; and contacting a surface of a press member against the outside surface of the medical device thereby pushing the active agent composition through the apertures and into the lumen of the medical device. Contacting the press member against the outside surface can include rolling the medical device against the press member. Contacting the press member against the outside surface can include rolling the press member against the medical device. The press member can contact multiple apertures at the same time. The press member can include a tube, the medical device disposed within the tube. The tube can include a flexible polymer. The method can further include placing the medical device within the press member, and placing the active agent within the press member. The method can further include disposing an actuation plate on the press member and moving the actuation plate back and forth in a direction perpendicular to a lengthwise axis of the medical device. In some embodiments, moving the actuation plate back and forth can be performed until the lumen is filled to at least about 90% of its capacity. The active agent composition can include a particulate material. The housing of the medical device can be coiled. In some embodiments, the plurality of apertures can provide the only fluid communication between the lumen and the outside of the medical device.

In some embodiments, the invention can include a system for filling the lumen of a medical device with an active agent. The system can include a tube having a first end and a second end; an actuation member having a surface that is flat in at least one direction, the actuation member configured to contact the tube; a drive unit coupled to the actuation member, the drive unit configured to move the actuation member back and forth causing the tube to roll back and forth. The system can further include an active agent composition and a medical device disposed within the tube, the medical device having a housing defining a lumen, the housing further defining a plurality of apertures providing fluid communication between the lumen and the outside surface of the medical device. The system can include a plurality of tubes having a first end and a second end, the plurality of tubes arranged parallel to one another. The system can further include a base plate, the tube sandwiched between the base plate and the actuation member. The drive unit can comprise an electric motor. The actuation member can exert a downward force on the tube.

In an embodiment, the invention can include a method of loading a medical device with an active agent. The method can include placing a medical device into a vessel, the medical device comprising an internal lumen and an exterior surface, the exterior surface defining a plurality of apertures connecting the internal lumen with the exterior surface; placing an active agent composition into the vessel; moving the vessel sufficiently to cause repeated contact between the medical device and the interior surface of the vessel, wherein such movement results in the active agent composition being forced into the internal lumen through the plurality of apertures. Moving the vessel can include rotating the vessel. The active agent composition can include particles. The operation of moving the vessel can be performed until the internal lumen is filled to at least about 90% of its capacity.

In an embodiment, the invention can include a system for filling the lumen of a medical device with an active agent. The system can include a vessel having a wall member; a drive unit coupled to the vessel, the drive unit configured to cause the vessel to move; an active agent composition disposed within the vessel; a medical device disposed within the vessel, the medical device having a housing defining a lumen, the housing having an exterior surface, the housing defining a plurality of apertures connecting the lumen with the exterior surface. The drive unit can include an electric motor.

In an embodiment, the invention can include a method of filling a medical device with an active agent. The method can include fluidizing a particulate active agent in a stream of air to form an active agent stream; channeling the active agent stream into a lumen within the medical device; allowing air from the active agent stream to escape the cavity while trapping the particulate active agent therein.

In an embodiment, the invention can include a system for filling the lumen of a medical device with an active agent. The system can include an air supply source; a fluidization chamber in fluid communication with the air supply source; an active agent composition disposed within the fluidization chamber; a conduit in fluid communication with the fluidization chamber; and a medical device comprising a housing defining a lumen, the housing having an exterior surface, the housing defining a plurality of apertures connecting the lumen with the exterior surface, the medical device in fluid communication with the conduit.

The invention claimed is:

1. A method of loading a medical device with an active agent, the method comprising:
   disposing an active agent in an interior volume of a fluidization chamber, wherein the interior volume of the fluidization chamber is in fluid communication with a first conduit and a second conduit;
   pumping air from an air supply source through the first conduit into the interior volume of the fluidization chamber;
   mixing the active agent with the air in the fluidization chamber to form a mixture;
   directing the active agent and air mixture into one or more apertures of a medical device via the second conduit, wherein the medical device comprises an outside surface and a lumen and one or more apertures connect the lumen to the outside surface; and
   depositing the active agent within the lumen of the medical device.

2. The method of claim 1, wherein pumping the air into the interior volume of the fluidization chamber causes turbulence within the interior volume of the fluidization chamber to mix the active agent with the air.

3. The method of claim 1, wherein some of the apertures of the medical device are at least partially occluded.

4. The method of claim 3, wherein some of the occluded apertures block passage of the active agent particles into the lumen while allowing air to flow through the lumen.

5. The method of claim 3, wherein one or more apertures are occluded by a porous sheath or mesh structure.

* * * * *